United States Patent [19]

Holtschmidt et al.

[11] 4,062,965
[45] Dec. 13, 1977

[54] QUATERNARY IMIDAZOLE COMPOUNDS AS MICROBICIDES

[75] Inventors: Ulrich Holtschmidt; Günter Schwarzmann, both of Essen, Germany

[73] Assignee: Th. Goldschmidt AG, Germany

[21] Appl. No.: 664,273

[22] Filed: Mar. 5, 1976

[30] Foreign Application Priority Data

Mar. 11, 1975 Germany ............................ 2510525

[51] Int. Cl.² ................... A61K 31/415; C07D 233/58
[52] U.S. Cl. .................................. 424/273 R; 548/335
[58] Field of Search .......................... 260/309; 424/273

[56] References Cited

U.S. PATENT DOCUMENTS

| 2,493,318 | 1/1950 | Shonle et al. ......................... 260/309 |
| 2,493,319 | 1/1950 | Shonle et al. ......................... 260/309 |
| 3,755,325 | 8/1973 | Clark et al. ........................... 260/309 |
| 3,853,907 | 12/1974 | Edwards ............................... 260/309 |

FOREIGN PATENT DOCUMENTS

43-12354  5/1968  Japan ..................... 260/309

OTHER PUBLICATIONS

Sawa et al. Chem. Abst. 1969, vol. 70, No. 11699f.
Monsanto Chem. Abst. 1951, vol. 45, cols. 10262–10263.
Shepard et al. J. Amer. Chem. Soc. 1947, vol. 69, pp. 2269–2270.

*Primary Examiner*—Natalie Trousof
*Attorney, Agent, or Firm*—James E. Bryan

[57] ABSTRACT

This invention relates to novel compounds having the formula:

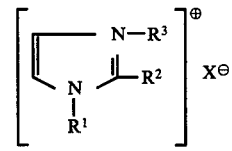

wherein $R^1$ is a straight-chain alkyl group having 8 to 18 carbon atoms, $R^2$ is a straight-chain alkyl group having 1 to 3 carbon atoms, $R^3$ is a straight-chain alkyl group having 8 to 16 carbon atoms, and X is chlorine or bromine. The invention further relates to novel microbiocidal compositions containing the novel compounds, and also to a process for preparing the novel compounds.

10 Claims, No Drawings

QUATERNARY IMIDAZOLE COMPOUNDS AS MICROBICIDES

The invention relates to new compounds of the general formula

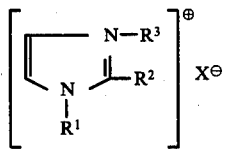

wherein $R^1$ is a straight-chain alkyl group with 8 to 18 carbon atoms, $R^2$ is a straight-chain alkyl group with 1 to 3 carbon atoms, $R^3$ is a straight-chain alkyl group with 8 to 16 carbon atoms, and X is chlorine or bromine. The invention also relates to processes for preparing these compounds and to microbiocidal compositions containing the compounds in effective amounts. The concept of a straight-chain alkyl group with 8 to 16 or 18 carbon atoms also includes a mixture of alkyl groups of varying chain lengths which on the average contain $C_8$ to $C_{16}$ or $C_{18}$ carbon atoms. Such mixtures of alkyl groups may be derived from fats occurring in nature. As a rule, therefore, the alkyl groups are even-numbered.

The developing and progressing technology of food preparation — be it in dairies, breweries, meat and sausage processing plants — but also the necessary disinfection in hospitals, baths and slaughter houses requires the preparation of highly effective compounds which, as much as possible, will combat not only bacteria, but also to the same extent bacteria, fungi and yeasts, and not only in inhibiting manner, but in a lethal manner. Because of the formation of resistant strains and natural selection, there is a constant need to prepare ever new means which in part will complement or excel older, tested products as regards effectiveness. The technical progress provided by finding new effective compounds must not absolutely reside in higher absolute effectiveness of the new compounds as compared to those of the state of the art. By their mere preparation, they allow an exchange for present disinfecting means and thereby decrease the formation of resistant strains. This alone already is appreciable technical progress.

However, beyond the feasibility of exchanging them against older disinfecting means, the new ones surprisingly are highly effective against bacteria, fungi and yeasts and therefore may be properly denoted as microbicidal compounds.

The new compounds of formula I are water-soluble and therefore may be prepared in a conventional manner. By such preparation is understood that of properly applicable substances, for instance aqueous solutions of the compounds of the invention in concentrated form or in such concentrations as are suitable for application. Therefore preparation also includes setting a specific pH value for a given application, and possibly also the addition of cationic or non-ionic known surfactants in order to reduce the boundary surface tension of the solutions and/or to increase their purification effects, possibly also to increase the coloring and/or scenting of the composition.

Another manner of preparation comprises making a dry product by using the crystalline pure substance or by mixing the pure substance with special inorganic inert carriers such as alkali phosphates or sulfates. Recently, the active materials have been dissolved in low-boiling solvents or solutions of the active materials have been sprayed by nitrogen under pressure. Such preparations are marketed as aerosols.

As discussed above, cationic or non-ionic surfactants may be added to the compounds of the invention. Suitable cationic compounds, for instance, are quaternary ammonium compounds such as cetyl pyridinium chloride which simultaneously possesses activity-enhancing properties. Non-ionic compounds may be adducts of ethylene oxide to compounds of acidic hydrogen, especially to alcohols with a chain length from 8 to 14 carbon atoms.

The optimum pH value for the applications under discussion ranges from slightly acidic to neutral and from about 4 to 8. Suitably weak organic acids, preferably acetic acid, should be used to adjust the desired pH value. However, polyfunctional acids such as citric or lactic acids are also suitable.

The new compounds of the invention may be prepared in known manner by reacting compounds of the formula

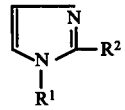

in a polar solvent, preferably a lower alcohol, with at least equimolar amounts of $R^3X$ at a temperature in the range of 80° to 150° C and in subsequently removing the solvent and if necessary the excess $R^3X$. Substituents $R^1$, $R^2$, $R^3$ and the X group are the same as in formula I.

Preferably the reaction will take place in the presence of excess $R^3X$. Removal of excess $R^3X$ compound appropriately is accomplished by distillation.

The following examples show the preparation in conformity with the invention of the compounds of the invention, and of the resulting microbiocidal preparations, and the microbiocidal properties of the latter.

Testing for microbiocidal properties follows along the guidelines from the DEUTSCHEN GESELLSCHAFT fur HYGIENE and MIKROBIOLOGIE (German Society for Sanitation and Microbiology), Gustav Fischer Publisher, Stuttgart, 1972. The symbol + denotes germ growth, while − indicates no growth.

EXAMPLE 1 a. Preparation of 1,3-di-n-dodecyl-2-methylimidazole bromide 0.5 mole of 1-n-dodecyl-2-methylimidazole is dissolved in 250 ml of i-propanol and reacted with 0.6 mole of n-dodecyl bromide. The reaction mixture is heated for 10 hours with reflux. Upon separation of the solvent, the remaining residue is washed with ether, suctioned off, and dried.

Yield: 217 grams.

| Elemental analysis for $C_{28}H_{55}N_2Br$: | | |
|---|---|---|
| | Computed % | Measured % |
| C | 67.2 | 67.1 |
| H | 11.1 | 11.3 |
| N | 5.6 | 5.6 |
| Br | 16.0 | 16.0 | b1. Preparation of the Microbiocidal Substance 10 parts by weight of 1,3-di-n-dodecyl-2-methylimidazole bromide, 10 parts of an adduct of 12 moles of ethylene oxide to 1 mole of i-tridecyl alcohol, 5 parts by weight of acetic acid and 75 parts by weight of water, are heated to 50° C and stirred. A clear, aqueous solution is obtained. This stock solution is diluted with water until a solution containing 0.1% by weight of the compound of the invention is obtained. The pH value is adjusted to 4.1 with acetic acid.

c1. Testing for Microbiocidal Effectiveness

| Test strain | Concentration in % | Time to act in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | − | − | − | − |
| E. coli | 0.1 | − | − | − | − | − | − |
| | 0.05 | − | − | − | − | − | − |
| | 0.01 | + | − | − | − | − | − |
| | 0.005 | + | + | + | + | + | − |
| | 0.001 | + | + | + | + | + | + |
| P. aeruginosa | 0.1 | − | − | − | − | − | − |
| | 0.05 | + | − | − | − | − | − |
| | 0.01 | + | + | + | + | − | − |
| | 0.005 | + | + | + | + | + | − |
| | 0.001 | + | + | + | + | + | + |
| G. candidum | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | − | − | − | − | b2. Preparation of the Microbiocidal Composition 6 parts by weight of 1,3-di-n-dodecyl-2-methylimidazole bromide, 4 parts by weight of a solution composed of 80% by weight of dodecyl-dimethyl-benzyl-ammonium bromide and 20% by weight of ethanol, 5 parts by weight of acetic acid and 84 parts by weight of water are stirred until the solution is clear. This stock solution is diluted with water until a solution containing 0.1% by weight of the bromide derivative of the invention is obtained. The pH value is adjusted to 7.8 by means of citric acid.

c2. Testing For Microbiocidal Effectiveness

| Test strain | Concentration in % | Time to act in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | − | − | − | − |
| E. coli | 0.1 | − | − | − | − | − | − |
| | 0.05 | − | − | − | − | − | − |
| | 0.01 | + | + | − | − | − | − |
| | 0.005 | + | + | + | + | + | − |
| | 0.001 | + | + | + | + | + | + |
| C. albicans | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | + | − | − | − | − |
| P. expansum | 0.1 | + | + | − | − | − | − |
| | 0.05 | + | + | − | − | − | − |
| | 0.01 | + | + | − | − | − | − |
| | 0.005 | + | + | − | − | − | − |
| | 0.001 | + | + | + | + | + | + |

EXAMPLE 2 a. Preparation of 1-n-dodecyl-2-methyl-3-n-octyl-imidazole bromide 1 mole of 1-n-dodecyl-2-methylimidazole is dissolved in 500 ml of n-propanol and reacted with 1.1 moles of n-octyl bromide. The reaction mixture is heated at 100° C for 5 hours. Upon removing the solvent, the remaining residue is washed with ether, suctioned off, and dried.

Yield: 204 grams.

| Elemental analysis for $C_{24}H_{47}N_2Br$: | | |
|---|---|---|
| | Computed % | Measured % |
| C | 65.0 | 64.0 |
| H | 10.7 | 10.4 |
| N | 6.3 | 6.4 |
| Br | 18.0 | 18.5 | b. Preparing the Microbiocidal Composition

One prepares a 0.1% by weight aqueous solution of the above compound and adjusts it to a pH value of 4.5 with acetic acid.

c. Testing For Microbiocidal Effectiveness

| Test strain | Concentration in % | Time to act in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | − | − | − | − | − |
| E. coli | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | + | + | − | − |
| P. vulgaris | 0.1 | − | − | − | − | − | − |
| | 0.05 | − | − | − | − | − | − |
| | 0.01 | − | − | − | − | − | − |
| | 0.005 | + | + | − | − | − | − |
| | 0.001 | + | + | + | + | − | − |
| P. aeruginosa | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | + | + | + | + |

EXAMPLE 3 a. Preparation of 1-n-hexadecyl-2-methyl-3-n-octyl-imidazole bromide 0.5 mole of 2-methyl-1-n-hexadecylimidazole is dissolved in 250 ml of i-propanol and reacted with 0.6 mole of n-octyl bromide. This is followed by a 10-hour boiling with reflux. Then the i-propanol is distilled off, together with the unreacted n-octyl bromide, and the remaining residue is washed with ether.

Yield: 221 grams.

| Elemental analysis: | | |
|---|---|---|
| | Computed % | Measured % |
| C | 67.3 | 67.2 |
| H | 11.1 | 11.0 |
| N | 5.6 | 5.7 |
| Br | 16.0 | 16.1 | b. Preparing the Microbiocidal Composition

A 0.1% by weight aqueous solution of the above compound is prepared and adjusted with acetic acid to a pH of 4.9.

c. Testing For Microbiocidal Effectiveness

| Test strain | Concentration in % | Time to act in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | + | − | − | − |
| E. coli | 0.1 | − | − | − | − | − | − |
| | 0.05 | − | − | − | − | − | − |
| | 0.01 | + | − | − | − | − | − |
| | 0.005 | + | + | + | + | − | − |
| | 0.001 | + | + | + | + | + | + |
| P. aeruginosa | 0.1 | − | − | − | − | − | − |
| | 0.05 | − | − | − | − | − | − |
| | 0.01 | + | + | + | − | − | − |
| | 0.005 | + | + | + | + | + | + |
| | 0.001 | + | + | + | + | + | + |
| P. expansum | 0.1 | + | + | − | − | − | − |
| | 0.05 | + | + | − | − | − | − |
| | 0.01 | + | + | − | − | − | − |
| | 0.005 | + | + | + | − | − | − |
| | 0.001 | + | + | + | + | − | − |

EXAMPLE 4 a. Preparation of 1,3-di-n-octyl-2-methyl-imidazole bromide 1 mole of 1-n-octyl-2-methylimidazole is dissolved with 1.1 moles of n-octyl bromide in 500 ml of n-propanol and heated at 105° C for 5 hours. Then, the n-propanol together with the unreacted n-octyl bromide is distilled off and the remaining residue is washed with ether.

Yield: 197 grams.

| | Elemental analysis for $C_{20}H_{39}N_2Br$: | |
|---|---|---|
| | Computed % | Measured % |
| C | 60.8 | 60.7 |
| H | 9.9 | 10.2 |
| N | 7.2 | 6.7 |
| Br | 20.2 | 19.6 | b. Preparing the Microbiocidal Composition

A 0.1% by weight aqueous solution of the above compound is prepared and adjusted to a pH of 6.7 with acetic acid.

c. Testing For Microbiocidal Effectiveness

| Test strain | Concentration in % | Time to act in minutes | | | | | |
|---|---|---|---|---|---|---|---|
| | | 1 | 2 | 5 | 10 | 20 | 30 |
| S. Aureus | 0.1 | − | − | − | − | − | − |
| | 0.05 | − | − | − | − | − | − |
| | 0.01 | + | + | + | + | − | − |
| E. coli | 0.1 | − | − | − | − | − | − |
| | 0.05 | − | − | − | − | − | − |
| | 0.01 | + | + | + | + | + | + |
| P. vulgaris | 0.1 | − | − | − | − | − | − |
| | 0.05 | − | − | − | − | − | − |
| | 0.01 | + | + | + | + | + | + |

EXAMPLE 5 a. Preparation of 1,3-di-n-octyl-2-ethyl-imidazole bromide 0.6 mole of 1-n-octyl-2-ethylimidazole is dissolved in 250 ml of i-propanol and 0.66 mole of n-octyl bromide are boiled with reflux for 5 hours. The alcohol then is separated and the remaining residue is washed with ether.

Yield: 202 grams.

| | Elemental analysis for $C_{21}H_{41}N_2Br$: | |
|---|---|---|
| | Computed % | Measured % |
| C | 62.9 | 62.8 |
| H | 10.3 | 10.7 |
| N | 6.9 | 6.9 |
| Br | 19.9 | 20.6 | b. Preparing the Microbiocidal Composition

A 0.1% by weight of aqueous solution is prepared and adjusted with acetic acid to a pH of 7.4.

c. Testing for Microbiocidal Effectiveness

| Test strain | Concentration in % | Time to act in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | + | + | + | − | − |
| | 0.005 | + | + | + | + | + | − |
| | 0.001 | + | + | + | + | + | + |
| G. candidum | 0.1 | − | − | − | − | − | − |
| | 0.05 | − | − | − | − | − | − |
| | 0.01 | + | + | + | − | − | − |
| | 0.005 | + | + | + | + | − | − |
| | 0.001 | + | + | + | + | + | + |
| P. expansum | 0.1 | − | − | − | − | − | − |
| | 0.05 | − | − | − | − | − | − |
| | 0.01 | + | + | + | + | − | − |
| | 0.005 | + | + | + | + | + | + |
| | 0.001 | + | + | + | + | + | + |
| T. mentagrophytes | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | − | − | − | − |

EXAMPLE 6 a. Preparation of 1,3-di-n-dodecyl-2-ethylimidazole bromide 0.38 mole of 1-n-dodecyl-2-ethylimidazole and 0.42 mole of n-dodecyl bromide are dissolved in 250 ml of ethanol and boiled with reflux for 5 hours. The solvent then is separated and the residue is washed with ether.

Yield: 190 grams.

| | Elemental analysis for $C_{29}H_{57}N_2Br$: | |
|---|---|---|
| | Computed % | Measured % |
| C | 67.8 | 66.8 |
| H | 11.4 | 11.2 |
| N | 5.4 | 4.9 |
| Br | 15.5 | 15.5 | b. Preparing the Microbiocidal Composition

A 0.1% by weight aqueous solution of the above compound is prepared and adjusted with acetic acid to a pH of 7.7.

c. Testing for Microbiocidal Effectiveness

| Test strain | Concentration in % | Time to act in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | − | − | − | − | − | − |
| | 0.005 | + | + | − | − | − | − |
| | 0.001 | + | + | + | + | − | − |
| E. coli | 0.1 | − | − | − | − | − | − |
| | 0.05 | − | − | − | − | − | − |
| | 0.01 | + | + | + | + | − | − |
| | 0.005 | + | + | + | + | + | + |
| | 0.001 | + | + | + | + | + | + |

-continued

| Test strain | Concentration in % | Time to act in minutes | | | | | |
|---|---|---|---|---|---|---|---|
| | | 1 | 2 | 5 | 10 | 20 | 30 |
| G. candidum | 0.1 | + | − | − | − | − | − |
| | 0.05 | + | − | − | − | − | − |
| | 0.01 | + | + | − | − | − | − |
| | 0.005 | + | + | − | − | − | − |
| | 0.001 | + | + | − | − | − | − |
| T. mentagrophytes | 0.1 | − | − | − | − | − | − |
| | 0.05 | − | − | − | − | − | − |
| | 0.01 | − | − | − | − | − | − |
| | 0.005 | + | + | − | − | − | − |
| | 0.001 | + | + | + | − | − | − |

EXAMPLE 7 a. Preparation of 1-n-dodecyl-2-ethyl-3-n-octyl-imidazole chloride 1 mole of n-dodecyl-2-ethylimidazole is dissolved in 500 ml of n-butanol and reacted with 1.2 moles of n-octyl chloride. This reaction mixture is heated at 127° C for 15 hours. Then the alcohol and the excess n-octyl chloride are distilled off and the remaining residue is washed with ether. Yield: 204 grams

| Elemental analysis for $C_{25}H_{49}N_2Cl$: | |
|---|---|
| | Computed % | Measured % |
| C | 72.7 | 72.2 |
| H | 11.9 | 11.9 |
| N | 6.7 | 7.0 |
| Cl | 8.6 | 8.9 | b. Preparing the Microbiocidal Composition

A 0.1% by weight aqueous solution of the above compound is prepared and adjusted with acetic acid to a pH of 7.3.

c. Testing for Microbiocidal Effectiveness

| Test strain | Concentration in % | Time to act in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | − | − | − | − | − | − |
| P. aeruginosa | 0.1 | − | − | − | − | − | − |
| | 0.05 | − | − | − | − | − | − |
| | 0.01 | − | − | − | − | − | − |
| | 0.005 | + | + | − | − | − | − |
| | 0.001 | + | + | + | + | + | + |
| C. albicans | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | − | − | − | − | − |
| T. mentagrophytes | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | − | − | − | − |

EXAMPLE 8 a. Preparation of 1-n-hexadecyl-2-ethyl-3-n-octyl-imidazole bromide 0.5 mole of 1-n-hexadecyl-2-ethylimidazole and 0.6 mole of n-octyl bromide are dissolved in 250 ml of i-propanol and boiled with reflux for 5 hours. The solvent then is separated and the residue washed with ether.

Yield: 233 grams.

| Elemental analysis for $C_{29}H_{57}N_2Br$: | |
|---|---|
| | Computed % | Measured % |
| C | 67.9 | 69.0 |
| H | 11.2 | 12.0 |
| N | 5.4 | 5.4 |
| Br | 15.5 | 14.8 | b. Preparing the Microbiocidal Composition

A 0.1% by weight aqueous solution of the above compound is prepared and adjusted with acetic acid to a pH of 7.2.

c. Testing for Microbiocidal Effectiveness

| Test strain | Concentration in % | Time to act in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | + | − | − | − | − | − |
| | 0.005 | + | + | − | − | − | − |
| | 0.001 | + | + | + | + | + | − |
| E. coli | 0.1 | − | − | − | − | − | − |
| | 0.05 | − | − | − | − | − | − |
| | 0.01 | + | + | + | − | − | − |
| | 0.005 | + | + | + | + | + | + |
| | 0.001 | + | + | + | + | + | + |
| G. candidum | 0.1 | + | + | − | − | − | − |
| | 0.05 | + | − | − | − | − | − |
| | 0.01 | + | + | − | − | − | − |
| | 0.005 | + | + | + | − | − | − |
| | 0.001 | + | + | + | − | − | − |

EXAMPLE 9 a. Preparation of 1-n-hexadecyl-2-n-propyl-3-n-octylimidazole bromide 1 mole of 1-n-hexadecyl-2-n-propylimidazole and 1.2 moles of n-octyl bromide are heated together at 150° C for 5 hours. Then the unreacted n-octyl bromide is distilled off and the residue is washed with ether.

Yield: 245 grams.

| Elemental analysis for $C_{30}H_{59}N_2Br$: | |
|---|---|
| | Computed % | Measured % |
| C | 68.2 | 68.6 |
| H | 11.3 | 10.4 |
| N | 5.3 | 5.1 |
| Br | 15.2 | 15.4 | b. Preparing the Microbiocidal Composition

A 0.1% by weight aqueous solution of the above compound is prepared and adjusted with acetic acid to a pH of 6.3.

c. Testing for Microbiocidal Effectiveness

| Test strain | Concentration in % | Time to act in minutes | | | | | |
|---|---|---|---|---|---|---|---|
| | | 1 | 2 | 5 | 10 | 20 | 30 |
| S. aureus | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | + | + | + | + | − |
| E. coli | 0.1 | − | − | − | − | − | − |
| | 0.05 | − | − | − | − | − | − |
| | 0.01 | + | − | − | − | − | − |
| | 0.005 | + | + | + | + | + | + |
| | 0.001 | + | + | + | + | + | + |
| P. aeruginosa | 0.1 | + | − | − | − | − | − |
| | 0.05 | + | − | − | − | − | − |
| | 0.01 | + | + | − | − | − | − |
| | 0.005 | + | + | + | + | + | + |
| | 0.001 | + | + | + | + | + | + |
| G. candidum | 0.1 | + | + | − | − | − | − |
| | 0.05 | + | + | − | − | − | − |

-continued

| Test strain | Concentration in % | Time to act in minutes | | | | | |
|---|---|---|---|---|---|---|---|
| | | 1 | 2 | 5 | 10 | 20 | 30 |
| | 0.01 | + | + | + | − | − | − |
| | 0.005 | + | + | + | − | − | − |
| | 0.001 | + | + | + | − | − | − |

It will be obvious to those skilled in the art that many modifications may be made within the scope of the present invention without departing from the spirit thereof, and the invention includes all such modifications.

What is claimed is:

1. A process for killing microbes which comprises contacting said microbes with a microbiocidally effective amount of a compound having the formula

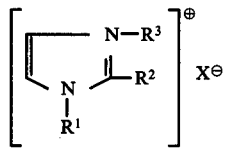

wherein $R^1$ is a straight-chain alkyl group having 8 to 18 carbon atoms, $R^2$ is a straight-chain alkyl group having 1 to 3 carbon atoms, $R^3$ is a straight-chain alkyl group having 8 to 16 carbon atoms, and X is chlorine or bromine.

2. A process according to claim 1 in which the compound has the formula 1,3-di-n-dodecyl-2-methyl-imidazole bromide.

3. A process according to claim 1 in which the compound has the formula 1-n-dodecyl-2-methyl-3-n-octyl-imidazole bromide.

4. A process according to claim 1 in which the compound has the formula 1-n-hexadecyl-2-methyl-3-n-octyl-imidazole bromide.

5. A process according to claim 1 in which the compound has the formula 1,3-di-n-octyl-2-methyl-imidazole bromide.

6. A process according to claim 1 in which the compound has the formula 1,3-di-n-octyl-2-ethyl-imidazole bromide.

7. A process according to claim 1 in which the compound has the formula 1,3-di-n-dodecyl-2-ethylimidazole bromide.

8. A process according to claim 1 in which the compound has the formula 1-n-dodecyl-2-ethyl-3-n-octyl imidazole chloride.

9. A process according to claim 1 in which the compound has the formula 1-n-hexadecyl-2-ethyl-3-n-octyl imidazole bromide.

10. A process according to claim 1 in which the compound has the formula 1-n-hexadecyl-2-n-propyl-3-n-octyl imidazole bromide.

* * * * *

UNITED STATES PATENT OFFICE
CERTIFICATE OF CORRECTION

Patent No. 4,062,965           Dated December 13, 1977

Inventor(s) Ulrich Holtschmidt and Günter Schwarzmann

It is certified that error appears in the above-identified patent and that said Letters Patent are hereby corrected as shown below:

Column 9, line 18, ",02/0020" should not appear therein.

Signed and Sealed this

Twenty-eighth Day of March 1978

[SEAL]

Attest:

RUTH C. MASON
*Attesting Officer*

LUTRELLE F. PARKER
*Acting Commissioner of Patents and Trademarks*